(12) United States Patent
Rontal

(10) Patent No.: US 10,806,482 B2
(45) Date of Patent: Oct. 20, 2020

(54) INTEGRATED PIEZOELECTRIC-DRIVEN VIBRATING BEAMS APPLICABLE TO HAND-HELD SURGICAL DEVICES

(71) Applicant: Michael Rontal, Farmington Hills, MI (US)

(72) Inventor: Michael Rontal, Farmington Hills, MI (US)

( * ) Notice: Subject to any disclaimer, the term of this patent is extended or adjusted under 35 U.S.C. 154(b) by 481 days.

(21) Appl. No.: 15/360,932

(22) Filed: Nov. 23, 2016

(65) Prior Publication Data

US 2017/0143367 A1 May 25, 2017

Related U.S. Application Data

(60) Provisional application No. 62/259,346, filed on Nov. 24, 2015.

(51) Int. Cl.
| | |
|---|---|
| *H01L 41/08* | (2006.01) |
| *A61B 17/32* | (2006.01) |
| *H01L 41/23* | (2013.01) |
| *A61B 17/00* | (2006.01) |

(52) U.S. Cl.
CPC ...... *A61B 17/320068* (2013.01); *H01L 41/08* (2013.01); *H01L 41/082* (2013.01); *H01L 41/23* (2013.01); *A61B 2017/00402* (2013.01); *A61B 2017/00526* (2013.01); *A61B 2017/320069* (2017.08); *A61B 2017/320073* (2017.08)

(58) Field of Classification Search
CPC ....... B06B 1/06; B06B 1/0603; B06B 1/0607; B06B 1/0633
USPC ......................... 310/322, 334, 335
See application file for complete search history.

(56) References Cited

U.S. PATENT DOCUMENTS

| | | | |
|---|---|---|---|
| 6,629,341 B2 * | 10/2003 | Wilkie | H01L 41/082 29/25.35 |
| 2006/0071580 A1 * | 4/2006 | Sawada | B06B 1/0633 310/369 |

* cited by examiner

*Primary Examiner* — Derek J Rosenau
(74) *Attorney, Agent, or Firm* — Law Offices of John G. Posa (57) ABSTRACT

A piezo-driven, vibrating beam is applicable to surgical procedures. A rod of piezoelectric material defines a length with proximal and distal ends. A pattern of electrodes, disposed adjacent to and along the length of the rod of piezoelectric material, is adapted for connection to a generator operative to stimulate the piezoelectric material, causing the rod to assume one or more vibratory states. In preferred embodiments, the proximal end of the rod of piezoelectric material is adapted for coupling to a blocking mass causing the vibratory states to be concentrated at the distal end of the rod of piezoelectric material. The pattern of electrodes may comprise interdigitated fingers, and the system may further include a material encapsulating the rod and the pattern of electrodes. Preferred embodiments may further include a plurality of coextensive, parallel rods forming a basic unit, each rod having a separate pattern of electrodes adjacent thereto.

9 Claims, 9 Drawing Sheets

INTEGRATED PIEZOELECTRIC-DRIVEN VIBRATING BEAMS APPLICABLE TO HAND-HELD SURGICAL DEVICES

CROSS-REFERENCE TO RELATED APPLICATIONS

This Application claims priority to U.S. Provisional Patent Application Ser. No. 62/259,346, filed Nov. 24, 2015, the entire content of which is incorporated herein by reference.

FIELD OF THE INVENTION

This invention relates generally to surgical devices and, in particular, to a surgical device powered by piezoelectric units to treat tissue.

BACKGROUND OF THE INVENTION

Ultrasound is a proven and useful energy source for surgical procedures. With it, tissue effects can be disintegration, cutting, coagulation, and treatment. These can be made to occur singly or in combination.

Present day tools use a design whereby a piezoelectric or magnetostrictive source produces the ultrasonic energy. A blocking device is attached to make the sound energy travel only in a proximal to distal direction. The distal end of the sound source is attached to a so called horn that condenses the sound energy into an attached waveguide. The waveguide may have a variety of specialized tips. The length of the waveguide is dictated by the wavelength of the sound so as to have the device tuned to the resonant frequency.

The action at the distal end is effected by actual movement of the tip in a variety of directions to cut, heat, coagulate, abrade, or sonically impact the tissue structure. A second effect is that the movement of the tip can be tuned to cause cavitation within a liquid medium. The vapor bubbles that cavitate will eventually implode. The release of the energy stored in the wall of the bubbles then acts on tissue, cells and associated molecules.

Because of the need for resonance, the size of the devices tends to be large and the power of these devices is high with heat production a significant factor. The devices tend to be straight line devices that are relatively heavy, ergonomically awkward with the waveguides being rigid and straight. This has reduced the application of ultrasonic surgical tools to more wide open surgical approaches where tissue does not obstruct the visualization of tip action. In addition, the application of the ultrasound is essentially in line with the longitudinal axis of the waveguide. these two problems reduces the applicability of ultrasound to surgical procedures.

U.S. Pat. No. 9,486,235, the entire content of which is incorporated herein by reference, describes a surgical instrument for treating body tissues through narrow body passages that employs an elongated cantilevered beam having a proximal end supported in a rigid block and a narrower distal end extendable through the narrow passages. One or more piezoelectric actuators are fixed to the beam surface and energized from an AC source through electrodes interspersed with the piezoelectric actuators to produce oscillatory motion of the beam distal end in multiple modes of movement with sensing electronics to monitor and control the distal mechanical movement.

The cantilevered beam, which may be made of metal or other materials, is generally flat. The flatness immediately reduces movement to the three planes, x, y and z. The energy source is operated at or near the proximal end with a blocker or stiffener to direct energy proximal to distal. The preferred energy source is a macro fiber composite (MFC) that is in various forms available commercially. One such set of MFCs available is made by Smart Materials, Inc.

These MFCs are flap coupon shaped devices that are in the range of 10×25 mm and 2-3 mm thick. This is a far smaller than the piezo ceramic wafer stack used in other devices. These MFCs are cemented to the flat surface with epoxy cements commercially available from many sources.

There is no horn or transducer involved as the shape of the beam or probe directly concentrates the sound energy. The tip of the probe is shaped for the effect desired. The flat shape of the probe divides the energy into x, y and z planes. The longitudinal axis plane is identified as the z plane, the transverse movement of the flat probe is identified as the y plane. There is little action in the x plane. By using a dual mode of excitation of various MFCs a dual mode movement is created to produce z and y action. This dual mode increases the spread of tip action or cavitation.

The cantilevered beam is a very efficient and ergonomic surgical device for working in narrow regions. An example would be deep in the nose. Though this probe may be bent, some regions may be difficult to reach if a short radius of bend is required. Also, the lengths of the probe are subject to the resonance action and restrict designs for certain regions. Finally, this design does not readily allow for any steering of the tip, as the probe is rigid.

SUMMARY OF THE INVENTION

This invention resides in a piezo-driven, vibrating beam applicable to surgical procedures including disintegration, cutting, coagulation, and treatment of biological tissues. In broad and general terms, the apparatus includes a rod of piezoelectric material having a length with proximal and distal ends. A pattern of electrodes, disposed adjacent to and along the length of the rod of piezoelectric material, is adapted for connection to a generator operative to stimulate the piezoelectric material, causing the rod to assume one or more vibratory states. In preferred embodiments, the proximal end of the rod of piezoelectric material is adapted for coupling to a blocking mass causing the vibratory states to be concentrated at the distal end of the rod of piezoelectric material.

The pattern of electrodes may comprise interdigitated fingers, and the system may further include a material encapsulating the rod and the pattern of electrodes. Preferred embodiments may further include a plurality of coextensive, parallel rods forming a basic unit, each rod having a separate pattern of electrodes adjacent thereto. Each rod may have a rectangular cross section, wherein a cross section of the basic unit shows two rows of two rods separated by one or more dielectric materials.

The pattern of electrodes may be deposited onto a sheet of dielectric material, with at least one rod being deposited onto the pattern of electrodes, in which case the sheet may be wrapped around the pattern of electrodes and the rod to form a protective sheath. The beam structure may further include a plurality of rods, each with a pattern of electrodes, and wherein the plurality of rods are encapsulated into a material providing a desired curved or bent shape. A surface or body may be included at the distal end of the rod configured to disintegrate, coagulate, cut or treat biological tissue.

A method of making a vibrating beam in accordance with the invention comprises the steps of: providing a first sheet of dielectric material; depositing an elongate pattern of electrodes onto the first sheet; depositing a rod of piezoelectric material on the elongate pattern of electrodes to form a beam having a length with proximal and distal ends; and wrapping the first sheet of dielectric material around the rod and electrodes to encapsulate the beam.

DETAILED DESCRIPTION OF THE INVENTION

This invention addresses outstanding concerns regarding piezo-driven cantilevered beams applicable to surgical and other uses. A point of novelty is that the energy source is no longer required to be at the proximal end of the probe. Rather, the invention exploits the flexible nature of macro fiber composite (MFC) rods by placing them directly within the probe. The probe then is free to be of rigid or flexible material. Now the probe can be of any length as resonance is not the determining factor. The system directs movement at the end of the PZT rods that make up the MFC such that energy is transmitted directly to the operating tip. As the PZT rods are bendable, essentially any angle from longitudinal axis is possible. As there is no need for resonance the walls of the probe can be flexible and thus the probe becomes steerable.

The actual rods are preferably in the range of 100 microns in diameter and of essentially any length. They are wrapped or encapsulated in a waterproof and electrically insulating dielectric material. Depending on the number of these basic units a device may or may not need heat dissipation. The guides for these basic units can be rigid (metal or a plurality of polymer materials) or flexible to create catheters and flexible devices that can be steered or floated through various channels such as vessels.

In accordance with the invention, interdigitated electrodes are disposed adjacent a rod of piezoelectric material. In preferred embodiments, the electrodes are electrically conductive material such as copper, and the piezoelectric material is PZT (lead zirconate titanate). The rods may have any cross-section shape though square or rectangular is preferred to provide an elongate flat surface against which the electrodes are bonded or adhered.

Figure 1:
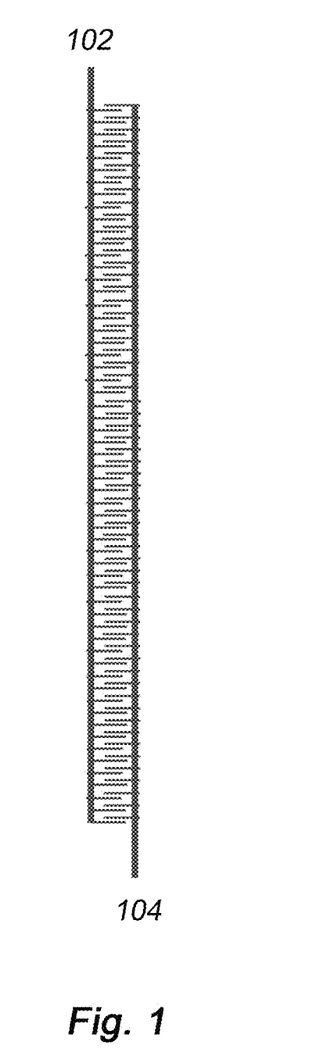
FIG. 1 is a drawing that shows two interdigitating electrode structures.

The Figures show the construction of a basic unit along with associated manufacturing steps. FIG. 1 shows two interdigitating units comprising finger-like electrode patterns 102, 104. The patterns may assume any operative potentials driven by generators of the types disclosed in U.S. Pat. No. 9,486,235, including one electrode being grounded while the other assumes an appropriate waveform, opposing positive-negative waveforms, and so forth. Such electrodes act as a virtual PZT wafer and a virtual stack, with each wafer elongated along the longitudinal axis of the rod, inducing a d33 mode, for example.

Figure 2:
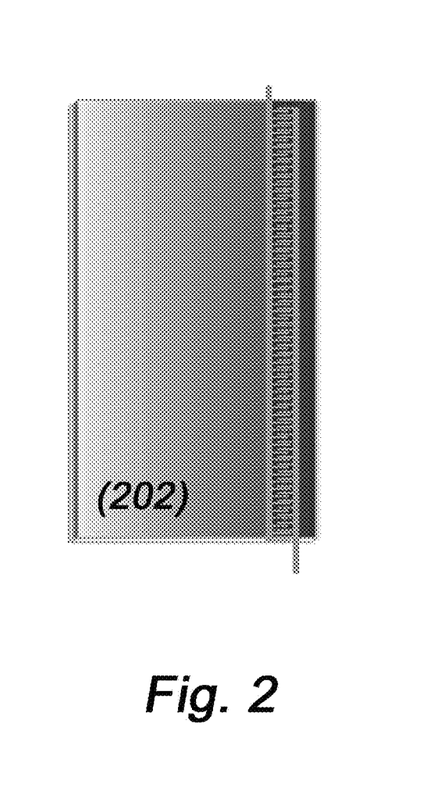
FIG. 2 illustrates excess PZT rod polyimide sheet trimmed in preparation for the wrapping; process.
Figure 3:
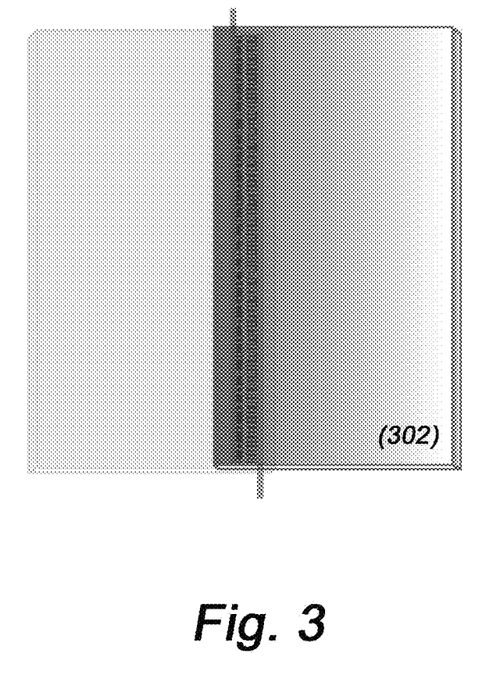
FIG. 3 shows a PZT sheet applied to electrode sheet forming interdigitated electrodes on PZT rods.
Figure 4:
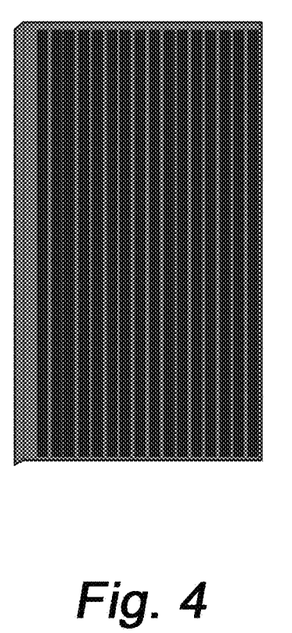
FIG. 4 depicts a solid wafer of PZT adhered to a flexible polyimide sheet, diced to ~100 microns.
Figure 5:
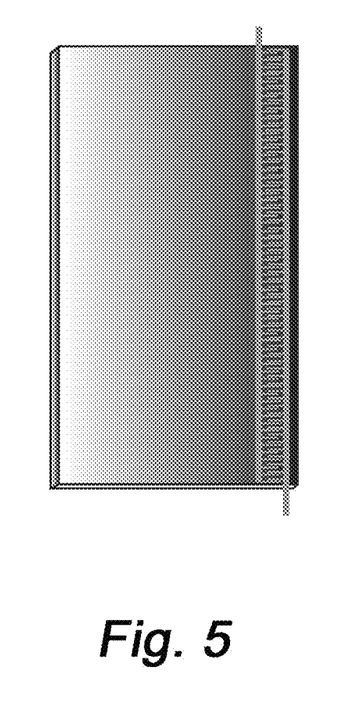
FIG. 5 illustrates interdigitated electrodes etched to polyimide sheet.
Figure 6:
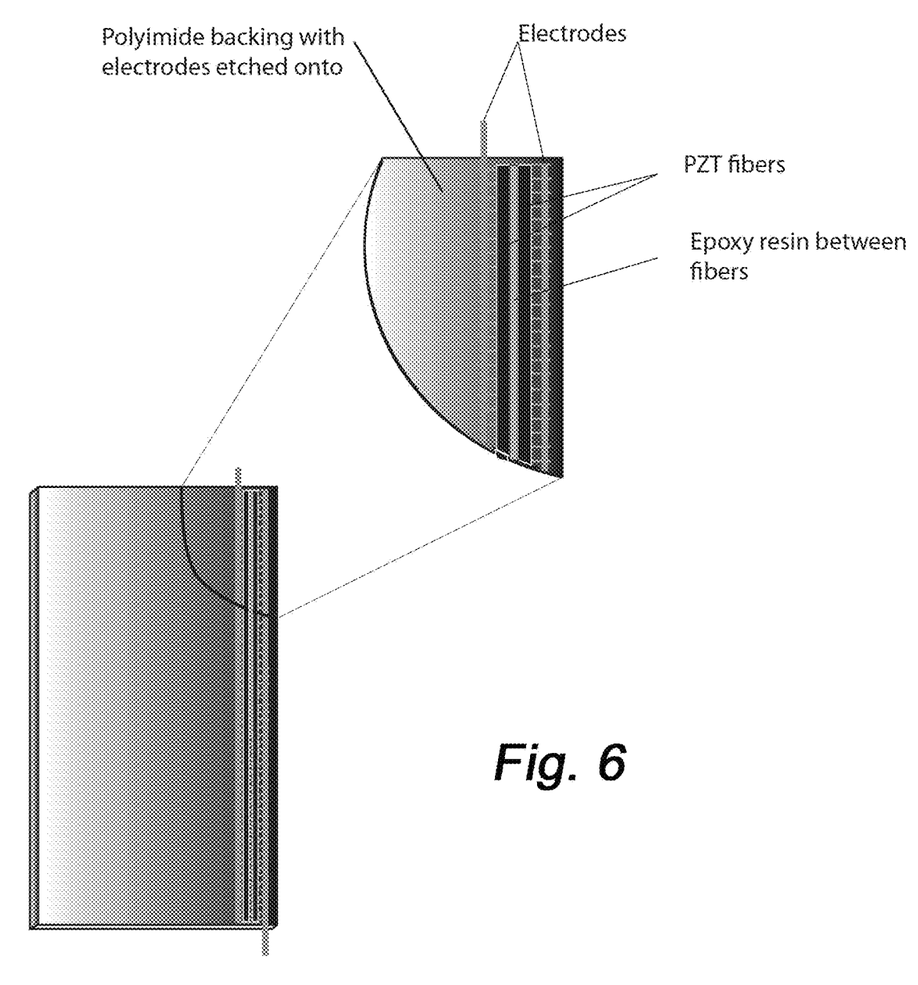
FIG. 6 shows the excess rods removed. Epoxy resin is provided between rods and a thin layer applied onto the rods.

FIG. 2 illustrates a polyimide sheet 202 trimmed in preparation for a wrapping process described in further detail below. FIG. 3 shows a PZT sheet 302 applied to the electrode sheet, forming interdigitated electrodes on PZT rods. FIG. 4 depicts a solid wafer of PZT material adhered to the flexible polyimide sheet, with the PZT sheet being diced to ~100 microns. FIG. 5 illustrates the interdigitated electrodes etched to polyimide sheet, and FIG. 6 shows the excess rods removed. Epoxy resin is provided between rods and thin layer applied onto the rods.

Figure 7:
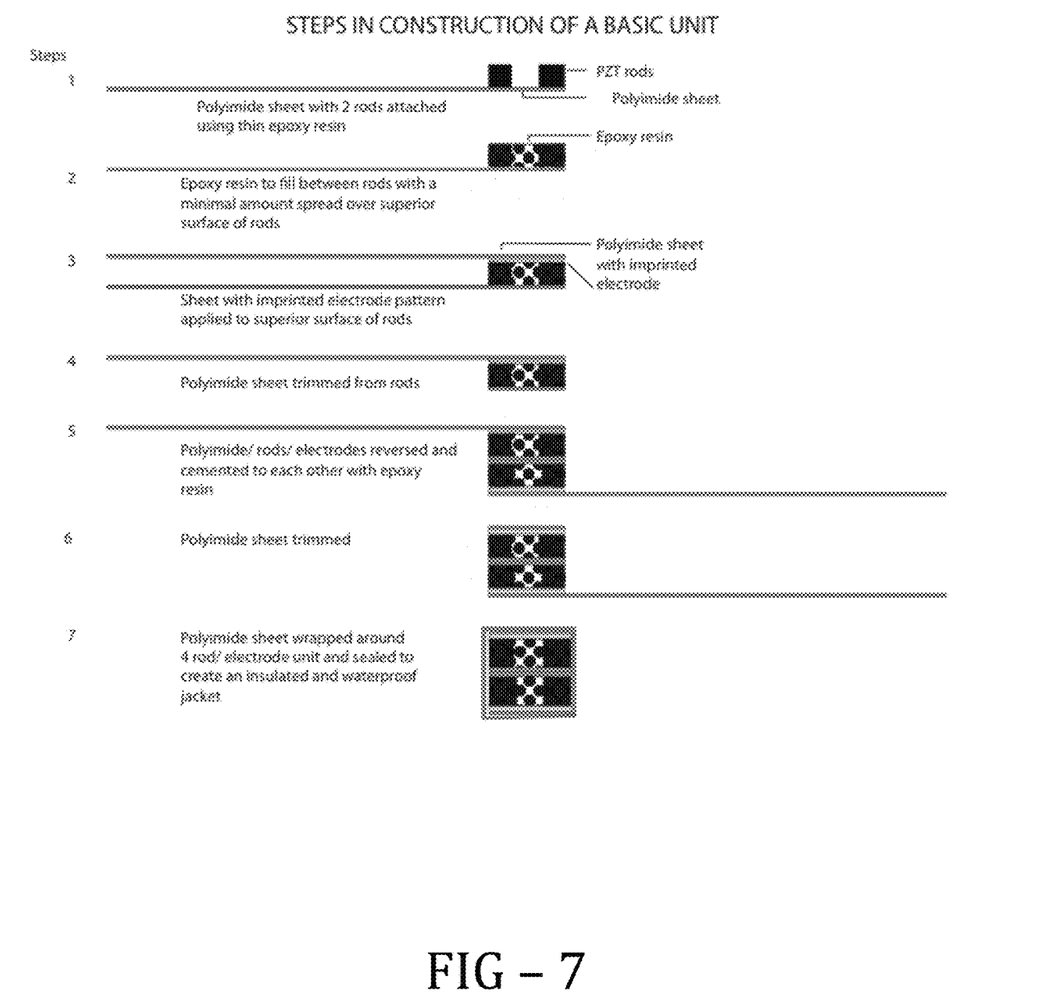
FIG. 7 shows steps associated with the construction of a basic unit.
Figure 8:
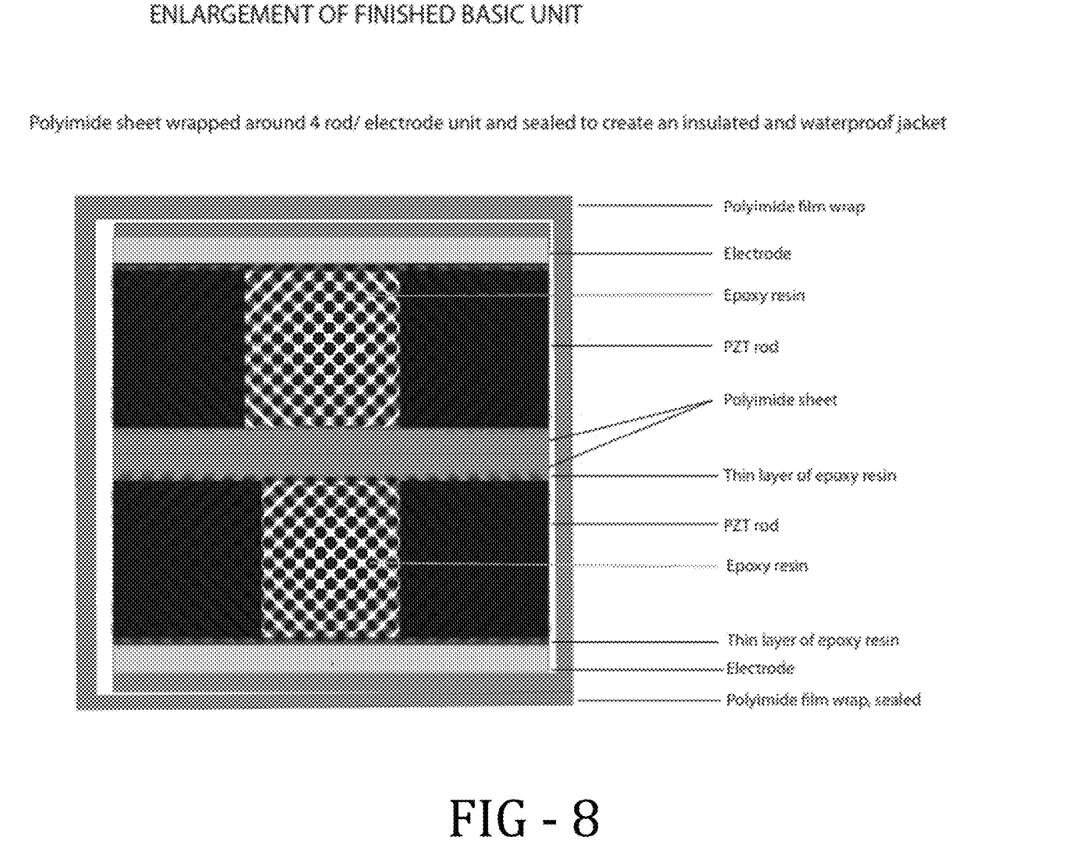
FIG. 8 is an enlarged cross section of a completed basic unit, in this case including four rods.
Figure 9A:
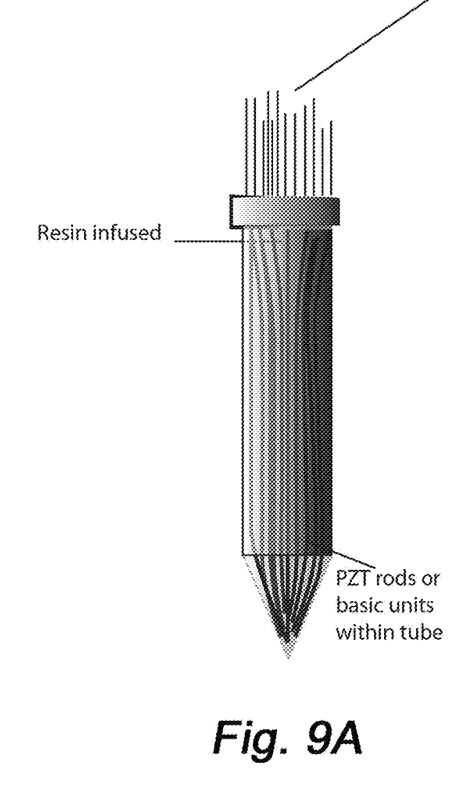
FIG. 9A illustrates a straight case with a sharp tip configured for tissue destruction and incising.
Figures 9B, 9C:
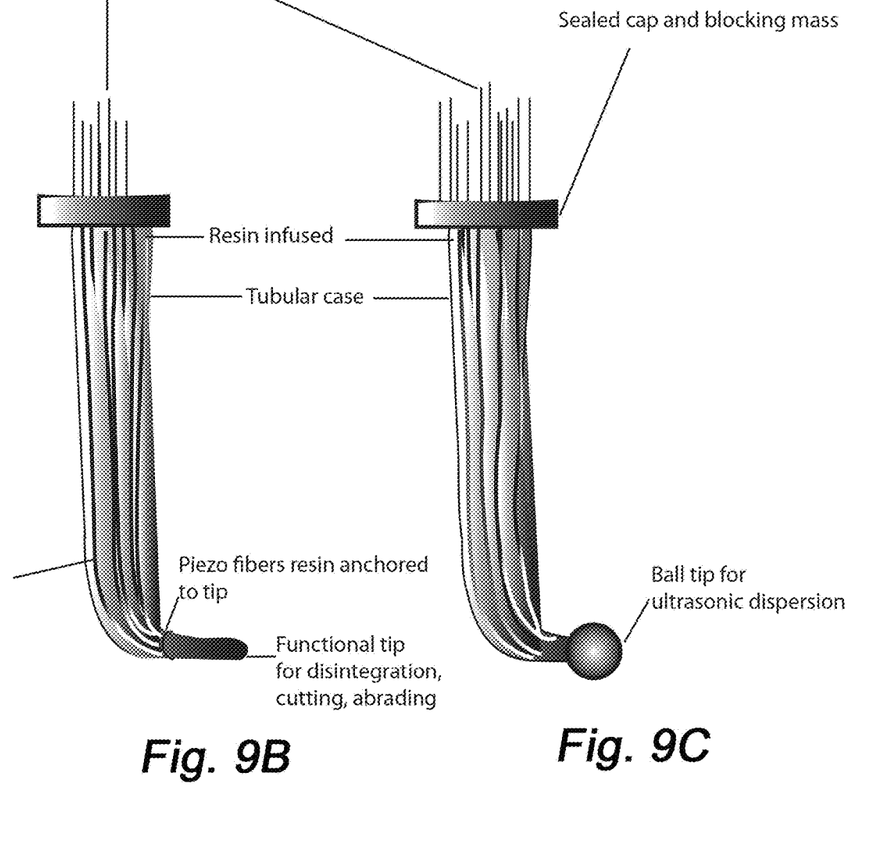
FIG. 9B shows a curved case including a tip configured for tissue destruction and incising.
FIG. 9C depicts a curved case with ball tip to disperse ultrasonic energy for therapeutic effects.

FIG. 7 shows steps associated with the construction of a basic unit, and FIG. 8 is an enlarged cross section of a completed basic unit, in this case including four rods. FIG. 9A illustrates a straight case with a sharp tip configured for tissue destruction and incising. FIG. 9B shows a curved case including a tip configured for tissue destruction and incising. FIG. 9C depicts a curved case with ball tip to disperse ultrasonic energy for therapeutic effects. The configurations of FIG. 9 are not meant to be limiting, and rather representative of potential case and tip designs, with the understanding that the case itself may be rigid or flexible depending upon the material(s) used for encapsulation.

The central core of the basic unit which is essentially filled with epoxy material can carry other features, as follows:

1. Graphene fabric/fibers or mesopitch carbon fiber can carry heat. Laid into this region and heat from the action of each fiber can be carried away from the site, exiting with the electrodes 2. The fibers as described already are acting in a d33 mode for accentuating longitudinal movement as the expansion contraction of poled PZT crystals are working in the same axis as the fiber (longitudinal). If an electrode runs down within the basic unit channel and the inside of the device is lined with an electrode plate a d31 action can be created. Here the fiber will expand and contract and on contraction from the sides will lengthen (like a toothpaste tube).

The invention claimed is:

1. A vibrating beam applicable to surgical procedures, comprising:
   a sheet of dielectric material;
   an elongated pattern of interdigitated electrodes deposited on the sheet of dielectric material;
   a flexible, bendable elongated rod of piezoelectric material having a length with proximal and distal ends;
   wherein the rod of piezoelectric material is bonded to the dielectric material such that the pattern of electrodes is disposed adjacent to and coextensively along the length of the rod of piezoelectric material; and
   wherein the pattern of electrodes is adapted for connection to a generator operative to stimulate the piezoelectric material, causing the rod to assume one or more vibratory states.

2. The vibrating beam of claim 1, further including a blocking mass coupled to the proximal end of the rod of piezoelectric material causing the vibratory states to be concentrated at the distal end of the rod of piezoelectric material.

3. The vibrating beam of claim 1, wherein the piezoelectric material is PZT (lead zirconate titanate).

4. The vibrating beam of claim 1, wherein:
the sheet of backing material is wider than the elongated rod; and
the sheet of backing material is folded around the rod so as to encapsulate the rod and the pattern of electrodes.

5. The vibrating beam of claim 1, further including a plurality of coextensive, parallel rods bonded to the backing material forming a basic unit, each rod having a separate pattern of electrodes adjacent thereto.

6. The vibrating beam of claim 5, further including four coextensive, parallel rods forming a basic unit;
wherein each rod has a rectangular cross section; and
wherein a cross section of the basic unit shows two rows of two rods.

7. The vibrating beam of claim 1, wherein
the sheet of dielectric material is wrapped around the pattern of electrodes and the rod to form a protective sheath.

8. The vibrating beam of claim 1, including a plurality of rods, each with a pattern of electrodes; and
wherein the plurality of rods are encapsulated into a material providing a desired curved or bent shape.

9. The vibrating beam of claim 1, further including a surface or body at the distal end of the rod configured to disintegrate, coagulate, cut or treat biological tissue.

* * * * *